(12) United States Patent
Stewart et al.

(10) Patent No.: US 10,048,230 B2
(45) Date of Patent: Aug. 14, 2018

(54) STRUCTURAL BOND INSPECTION

(71) Applicant: The Boeing Company, Chicago, IL (US)

(72) Inventors: Alan F. Stewart, Seattle, WA (US); Hong H. Tat, Redmond, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 361 days.

(21) Appl. No.: 14/080,753

(22) Filed: Nov. 14, 2013

(65) Prior Publication Data

US 2015/0128709 A1     May 14, 2015

(51) Int. Cl.
| | |
|---|---|
| *G01N 29/11* | (2006.01) |
| *G01N 29/04* | (2006.01) |
| *G01N 29/14* | (2006.01) |
| *G01N 19/04* | (2006.01) |

(52) U.S. Cl.
CPC ........... *G01N 29/11* (2013.01); *G01N 29/045* (2013.01); *G01N 29/14* (2013.01); *G01N 19/04* (2013.01); *G01N 2291/0231* (2013.01); *G01N 2291/2694* (2013.01)

(58) Field of Classification Search
CPC ....... G01N 29/11; G01N 29/14; G01N 29/045
USPC .......................................... 73/588, 643, 587
See application file for complete search history.

(56) References Cited

U.S. PATENT DOCUMENTS

| | | | | |
|---|---|---|---|---|
| 3,512,400 | A | * | 5/1970 | Lynnworth .......... G01N 29/041 73/597 |
| 4,121,470 | A | * | 10/1978 | Kaule ...................... G01H 9/00 356/502 |
| 4,584,879 | A | * | 4/1986 | Webster ................. G01N 29/14 73/588 |
| 6,386,038 | B1 | * | 5/2002 | Lewis, III .............. G01N 29/14 702/39 |
| 6,622,568 | B2 | | 9/2003 | Nelson et al. |
| 6,848,321 | B2 | | 2/2005 | Bossi et al. |
| 6,865,948 | B1 | * | 3/2005 | Chen .................. G01N 21/9503 250/559.42 |
| 7,507,312 | B2 | | 3/2009 | Bossi et al. |
| 7,509,876 | B1 | | 3/2009 | Sokol et al. |

(Continued)

FOREIGN PATENT DOCUMENTS

| | | |
|---|---|---|
| JP | 2005300273 | 10/2005 |
| KR | 101179134 | 9/2012 |

OTHER PUBLICATIONS

Kobayashi et al., Evaluation of shot peening by AE method, Sintokogio, Ltd., www.sinto.co.jp, 4th International Conference on Laser Peening and Related Phenomena, May 2013, Madrid Spain.

(Continued)

*Primary Examiner* — Lisa Caputo
*Assistant Examiner* — Tarun Sinha
(74) *Attorney, Agent, or Firm* — Kunzler, PC

(57) ABSTRACT

A method for determining the presence of damage in a structure includes applying energy to the structure to induce tension shockwaves in the structure. The method also includes detecting sound waves caused by the tension shockwaves using at least one acoustic emission sensor on the surface of the structure. Additionally, the method includes determining the presence of damage in the structure due to the applied energy based on detected sound waves.

19 Claims, 6 Drawing Sheets

(56) References Cited

U.S. PATENT DOCUMENTS

| | | | |
|---|---|---|---|
| 7,735,377 B1 | 6/2010 | Sokol et al. | |
| 7,770,454 B2* | 8/2010 | Sokol | G01N 29/2412 |
| | | | 73/588 |
| 8,225,664 B1 | 7/2012 | Sokol et al. | |
| 2004/0020298 A1* | 2/2004 | Siverling | G01N 29/275 |
| | | | 73/644 |
| 2004/0025593 A1* | 2/2004 | Hashimoto | G01N 17/006 |
| | | | 73/643 |
| 2005/0120803 A1* | 6/2005 | Sokol | G01N 29/2412 |
| | | | 73/801 |
| 2006/0179949 A1* | 8/2006 | Kim | G01H 9/004 |
| | | | 73/588 |
| 2011/0314915 A1* | 12/2011 | Adams | G01M 5/0033 |
| | | | 73/582 |
| 2015/0033864 A1* | 2/2015 | Kumar | G01N 29/265 |
| | | | 73/636 |

OTHER PUBLICATIONS

Enoki et al., Quantitative Acoustic Emission Measurement of Laser Peening, 30th European Conference on Acoustic Emission Testing & 7th International Conference on Acoustic Emission, University of Granada, Sep. 12-15, 2012.

Ito et al., Acquisition and Analysis of Continuous Acoustic Emission Waveform for Classification of Damage Sources in Ceramic Fiber Mat, Materials Transactions, vol. 48 No. 06, pp. 1221-1226, 2007.

Raju et al., Characterization of Defects in Graphite Fiber Based Composite Structures Using the Acoustic Impact Technique (AIT), Journal of Testing and Evaluation, 1993, pp. 337-395, vol. No. 5, Philadelphia, PA, US.

International Search Report, Application No. PCT/US2014/059596, dated Feb. 3, 2015.

* cited by examiner

US 10,048,230 B2

STRUCTURAL BOND INSPECTION

FIELD

This disclosure relates to inspecting the structural integrity of a bond of a structure and more particularly relates to detecting the presence of defects in a bond using an acoustic emission technique to analyze testing-induced disbonds in the structure.

BACKGROUND

There are many systems and methods for testing the strength of an adhesive bond between two materials of a structure. Some systems and methods are designed to detect the strength of an adhesive bond in a non-destructive manner while the bond is in situ or intact. For example, laser bond inspection techniques can be used to detect the strength of an adhesive bond by transmitting a laser-induced stress wave through the bonded structure. The stress waves are initiated at a top surface as compression waves that convert into tension waves upon reflecting off of a second free surface of the structure (which can be a bottom surface). The tension waves apply opposing tension forces onto the two materials forming the bond to effectively pull apart the materials along the bond.

Various conventional surface motion detectors may be used to detect the motion of the surfaces during a laser bond inspection process. For example, electromagnetic acoustic transducers (EMAT) and a velocity interferometer system for any reflector (VISAR) are available for detecting the motion of the surfaces of bonded materials. EMAT transducers use a magnet and a coil to detect motion of a conductive foil adhered to the surface of the bonded material. In one application, the EMAT sensor detects an electric current in the conductive foil due to the stress wave induced motion of the foil in the magnetic field.

Depending on the strength of the bond, the application of a laser-induced stress wave into bonded materials may create defects in the structure. These defects will occur at the weakest part of the structure often in the form of a separation or disbond at the bondline or delamination in the composite structure itself. Disbonds are a separation of the previously bonded surfaces, which can be detected using conventional ultrasound. Accordingly, the detection of such disbonds after a laser bond inspection process may be desirable. Some ultrasonic inspection techniques are available to detect the presence of disbonds within a bonded material. Ultrasonic inspection techniques include using ultrasonic transducers to impart a vibration into a material and measure the resultant feedback vibration. Depending on the characteristics of the feedback vibration, a user can identify locations in the material where the bond has abnormalities or defects. Some ultrasonic techniques are performed using a hand probe. However, such ultrasonic techniques do not provide precise results or results with a high level of detail. For more precise results, many ultrasonic inspection techniques employ an immersion tank and scanning bridge, with the bonded materials being tested submersed in the immersion tank.

SUMMARY

The subject matter of the present disclosure has been developed in response to the present state of the art, and in particular, in response to the limitations of conventional structural bond testing systems. Specifically, conventional structural bond testing systems that induce stress waves within a bonded material (e.g., laser bond inspection systems) to detect the strength of a bond do not allow for the precise, accurate, and direct identification of disbonds or interlaminate failure while the stress wave is propagating through the material during the testing process. Some techniques used in conjunction with conventional structural bond testing systems, such as EMAT and velocity interferometer techniques, are used to detect motion of the surfaces of a bonded material, and may be used to indirectly identify disbonds. These techniques are relatively imprecise and inaccurate, or difficult to implement. Other techniques specifically configured to identify disbonds, such as ultrasonic inspection techniques, are conducted after stress wave testing has concluded and often employ cumbersome and non-transportable testing equipment, both resulting in reduced efficiency and increased costs. Accordingly, the subject matter of the present disclosure has been developed to provide an apparatus, system, and method for detecting or identifying abnormalities or damage (e.g., disbonds or interlaminate failures) in a bond that overcome at least some of the above-discussed shortcomings of the prior art.

According to one embodiment, a method for determining the presence of damage in a structure (e.g., a bonded structure) includes applying energy to the structure to induce tension shockwaves in the structure. The method also includes detecting sound waves caused by the tension shockwaves using at least one acoustic emission sensor on the surface of the structure. Additionally, the method includes determining the presence of damage in the structure due to the applied energy based on detected sound waves.

In some implementations of the method, detecting the sound waves includes detecting frequency characteristics of the sound waves, and determining the presence of damage in the structure is based on detected frequency characteristics of the sound waves. The frequency characteristics can include a change in a characteristic frequency associated with the structure when no damage is present, and where the presence of the change in the characteristic frequency indicates damage in the structure.

In certain implementations, the method includes estimating expected sound waves based on characteristics of applied energy to the structure. Determining the presence of damage in the structure may include comparing the expected sound waves with detected sound waves.

According to yet certain implementations of the method, applying energy to the structure includes controlling characteristics of the energy such that the tension shockwaves have a frequency less than about 10 MHz. The characteristics of the energy may be controlled such that the tension shockwaves have a frequency less than about 5 MHz. The detected sound waves are analyzed to produce a Fast Fourier Transform pattern, which can be a spectrum.

In some implementations of the method, at least one acoustic emission sensor is one of fixedly secured to the structure or movable along the surface of the structure. Applying energy to the structure can induce compression shockwaves. The compression shockwaves may convert into the tension shockwaves upon reflection off a surface of the structure. According to certain implementations, the energy includes at least one laser beam.

In yet some implementations, the method includes assessing a minimal strength of the structure based on the determination of whether damage in the structure is present. Damage in the structure can include a disbond or delamination. The structure may include first and second layers each made from a composite material or a composite material and a metal. In some implementations, disbonds can be defined as separation of an adhesive layer between and adjoining the first and second layers. Further, the separation can be within the adhesive itself or between the adhesive and adjoining layers.

According to certain implementations of the method, applying energy to the structure includes applying a first low energy to the structure to induce first tension shockwaves, applying a second high energy to the structure to induce second tension shockwaves, and applying a third low energy to the structure to induce third tension shockwaves. Detecting sound waves can include detecting first sound waves caused by the first tension shockwaves, second sound waves caused by the second tension shockwaves, and third sound waves caused by the third tension shockwaves. Further, determining the presence of damage in the structure due to the applied energy can include comparing the first sound waves to the third sound waves. A variation between a frequency pattern of the first sound waves and a frequency pattern of the third sound waves may indicate the presence of damage in the bonded structure. As defined herein, a frequency pattern can include a frequency spectrum.

In another embodiment, a system is disclosed for concurrently determining (e.g., validating) the strength of a bonded structure and presence of disbonds in the bonded structure. The system includes a wave induction tool that induces a shockwave in the bonded structure. Additionally, the system includes a sound wave sensing device that detects a sound wave induced by the shockwave. The sound wave sensing device is in direct contact with a surface of the bonded structure. The system further includes a controller that determines the presence of disbonds in the bonded structure based on characteristics of the sound wave detected by the sound wave sensing device. The controller can further determine a minimum strength (e.g., validate the strength) of the bonded structure based on the presence of disbonds in the bonded structure.

According to some implementations of the system, the wave induction tool is movable along a surface of the bonded structure and the sound wave sensing device is non-movably coupled to a surface of the bonded structure. The wave induction tool and the sound wave sensing device are movable along a surface of the bonded structure in one implementation. The sound wave sensing device can include at least two acoustic emission sensors, where the acoustic emission sensors are positioned on a surface of the bonded structure. In certain implementations, a first of the acoustic emission sensors is a first distance away from a shockwave induction region in the bonded structure and a second of the acoustic emission sensors is a second distance away from the shockwave induction region. The first distance can be different than the second distance. The strength of the bonded structure may correspond with a strength of the shockwave necessary to create a disbond in the bonded structure.

In yet another embodiment, an apparatus is disclosed for concurrently testing the strength of a bonded structure and determining the presence of disbonds in the bonded structure. The apparatus includes a laser bond inspection module and an acoustic emission detection module. The laser bond inspection module is configured to command a transmission of a laser beam onto the bonded structure to induce a shockwave in the bonded structure. The apparatus includes at least one acoustic emission sensor in contact with a surface of the bonded structure. The acoustic emission detection module is configured to determine the presence of a disbond in the bonded structure and verification of the strength of the bond based on at least one frequency characteristic of a sound wave in the bonded structure induced by the shockwave. The sound wave is detected by the at least one acoustic emission sensor. The acoustic emission detection module can be configured to determine the presence of a disbond in the bonded structure based on at least one characteristic of the laser beam transmitted onto the bonded structure.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Figure 1:
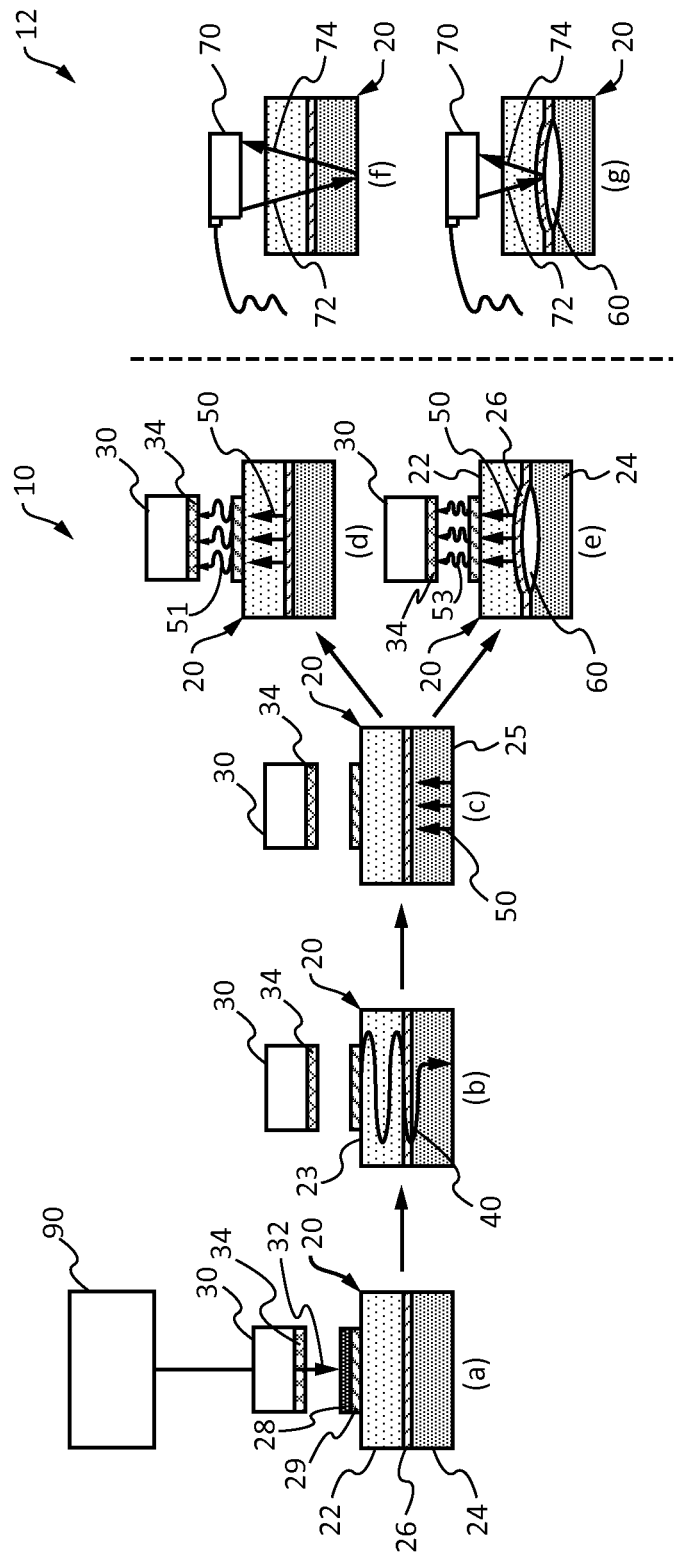
FIG. 1 is a schematic flow diagram of a conventional laser bond inspection process and an ultrasound inspection sub-process according to the prior art.

Referring to FIG. 1, a conventional bond inspection process 10 includes a wave induction tool 30 that transmits energy onto a structure 20 being tested to induce a stress wave or shockwave in the materials forming the structure. In the illustrated implementation, the wave induction tool 30 is a laser-generating tool that generates a high-energy laser beam 32 and directs the laser beam onto the structure 20.

In the illustrated embodiment, the structure 20 includes at least two layers 22, 24 of material bonded together by an adhesive layer 26. The adhesive layer 26 forms a bond between the layers 22, 24 of the structure 20 to effectively fixedly couple the layers together or join the layers to each other. The layers 22, 24 can be made from any of various materials, such as, for example, metals, composites, plastics, ceramics, and the like. The adhesive layer 26 can be made from any of various adhesives, such as emulsion adhesives, pressure sensitive adhesives, contact adhesives, hot adhesives, reactive adhesives, such as acrylics, urethanes, and epoxies, natural adhesives, and synthetic adhesives, such as elastomers, thermoplastics, emulsions, and thermosets. In one specific implementation, the layers 22, 24 are made from a fiber-reinforced polymer composite material and the adhesive layer 26 is made from an epoxy or thermoset adhesive.

Referring to FIG. 1(a), the wave induction tool 30 generates an internal stress wave within the structure 20 by directing a controlled and pulsed beam of energy onto the surface of the structure. In one embodiment, the wave induction tool 30 is a laser-generated wave induction tool 30 that generates and transmits a laser beam 32 having controlled characteristics at the structure 20. The characteristics, such as pulse duration and magnitude, can be controlled by a controller 90.

The impact of the laser beam 32 on the surface of the structure 20 induces compression shockwaves 40 that propagate through the structure as shown in FIG. 1(b). The compression shockwave 40 propagates from a front surface 23 (e.g., the surface impacted by the beam of energy) to a back surface 25 that opposes the front surface. Upon reaching the back surface 25 of the structure 20, the compression shockwave 40 reflects off of the back surface as a tension shockwave 50 as shown in FIG. 1(c). In other words, reflection off the back surface 25 of the structure 20 converts the compression shockwave 40 into a tension shockwave 50. The frequency and magnitude of the compression and tension shockwaves 40, 50 are based on the pulse duration and irradiance of the energy impacting the surface of the structure 20 as controlled by the controller 90. The tension shockwave 50 propagates from the back surface 25 to the front surface 23 of the structure 20 as shown in FIGS. 1(d) and 1(e). In one implementation, the conventional bond inspection process 10 also utilizes a surface-velocity sensing device 34 that is spaced apart from the front surface 23 and detects the surface velocity or motion 51, 53 of a foil loop 29 bonded to the front surface 23. In other words, the surface-velocity sensing device 34 is not in contact with the surface 23 of the structure 20, but is spaced-apart from the surface. The surface velocity measurement by the sensing device 34 forms the basis for a verification of the strength of the bond. For example, in some implementations, the controller 90 utilizes the surface velocity measurement from the sensing device 34 to verify that the bond remains intact. However, due to the lower sensitivity of the off-surface velocity sensing device 34, the surface velocity measurements obtained by the sensing device 34 and the associated bond strength estimations are inefficient and often inaccurate.

The sensing device 34 is any of various off-surface surface-velocity sensing devices known in the art, such as, for example, electromagnetic acoustic transducers (EMAT) and velocity interferometers. EMAT velocity sensing devices require a conductive material moving in a magnetic field to produce a measurable current. In one embodiment, the conductive foil loop 29 is placed on the surface of the structure 20 between the EMAT velocity sensing device 34 and the structure. Typically, such conductive foil loops 29 are formed on tape, which is adhered to the surface of the structure 20. A conductive foil loop 29 may also be screen printed or otherwise deposited on the surface of the structure. Unfortunately, conductive foil loops 29 are expensive to fabricate and the placement and application of conductive foil loops onto the structure necessitate an additional and time-consuming step to the conventional bond inspection process 10. Further, as shown, the sensing device 34 is traditionally positioned on the head of the wave induction tool 30, which results in a larger than desirable head and reduces the flexibility where the sensing device can be located relative to the structure 20.

Although shown spaced apart from the front surface 23 of the structure 20 and foil loop 29 for detecting the surface velocity of the structure at the front surface, the surface-velocity sensing device 34 can also, or alternatively, be spaced apart from the back surface 25 for detecting the surface velocity of the structure at the back surface. The surface velocity measurement at the back surface can then form the basis for estimating the strength of the bond in the same way as the front surface. For example, a velocity interferometer can be placed near the back surface of the structure 20 to detect surface velocities at the back surface, which can be used as a basis for estimating the strength of the bond.

Further, although in the illustrated embodiment, the wave induction tool 30 is a laser wave induction tool, the wave induction tool can be any of various other devices configured to induce shockwaves in the structure. In some implementations, the wave induction tool 30 can be a mechanical wave induction tool that imparts energy to the structure via a projective impact technique, such as striking the structure with a hammer or other pinging device. In other implementations, the wave induction tool may be a hydroshock wave induction tool that imparts energy to the structure via a hydroshock impact technique. Further, the wave induction tool 30 may be configured to induce tension shockwaves directly in the structure 20, as opposed to generating compression shockwaves that convert into tension shockwaves. In other implementations, the wave induction tool 30 may generate a single pulse from an electric field, a pulse of electric current, a pulse from a magnetic field, and induction current loading.

The wave induction tool 30 can be a hand-operated tool that is manually movable about a surface of the structure 20. For example, the wave induction tool 30 may be similar to the wave induction tool shown in FIG. 3. In some implementations, the hand-operated tool integrates the features of the surface-velocity sensing device 34. For example, the wave induction tool 30 may include a head that incorporates an energy transmitting portion and a surface-velocity sensing portion.

To facilitate the receipt of energy from the wave induction tool 30 and transmission of resultant shockwaves through the structure 20, an ablative layer 28 can be positioned on the structure between the wave induction tool and the surface 23 of the structure. The ablative layer 28 receives the impact of the energy and absorbs the energy such that damage to and heating of the structure 20 is reduced. The ablative layer 28 can be a layer of paint, tape, or other expendable material. In some implementations, a tamping layer (e.g., water) can be used to facilitate the transmission of energy into the surface of the structure 20.

Referring to FIGS. 1(c)-(e), the tension shockwave 50 applies a proof test load to the bond formed by the adhesive layer 26 between the layers 22, 24 of the structure 20. The load tends to pull the layers 22, 24 away from each other along a bondline defined by the interface between the adhesive layer 26 and the layers 22, 24. At locations along the bondline where the bond is strong, the strength of the bond resists the separation of the layers 22, 24 (see, e.g., FIG. 1(d)). However, at locations along the bondline where the bond is weak, the strength of the bond is unable to resist separation of the layers 22, 24, and the layers separate along the bondline to form a pocket or disbond 60 between the layers (see, e.g., FIG. 1(e)). Generally, the disbond 60 is a localized area of the bond where the adhesive layer 26 has separated from or become unadhered from an adjoining one or more of the layers 22, 24. Accordingly, a disbond may be defined as a localized delamination of bonded surfaces. In the illustrated embodiment of FIG. 1(e), the disbond 60 is formed due to the adhesive layer 26 becoming separated from the layer 24, while remaining adhered to the layer 22. However, in other implementations, the disbond 60 is formed when the adhesive layer 26 separates from the layer 22, while remaining adhered to the layer 24. Alternatively, the disbond 60 can be formed when the adhesive layer 26 separates from both the layers 22, 24. Also, in some cases, the tension shock wave may cause a disbond within the adhesive layer. Accordingly, the step of inducing shockwaves in the conventional bond inspection process 10 for determining the strength of a bond in a bonded structure 20 can also cause delamination or disbonding of the bonded structure. As defined herein, a bonded structure is any structure or object with at least two layers, materials, or sub-structures bonded together by an adhesive.

As a composite material of a structure is typically fabricated from many composite layers each bonded to each other, disbonds can also form within the composite material of the structure between layers of the composite material. These types of disbonds can be defined as interlaminar disbonds. The tension wave producing the disbond will create a disbond at the location in the structure with the lowest strength, which can be the laminate within a composite material or the bondline of a bond between two separate pieces of composite materials or in the adhesive itself.

Although the combination of the wave induction tool 30 and the off-surface surface-velocity sensing device 34 may be useful in estimating the strength of the bond in the bonded structure 20, the combination is unable to accurately, efficiently, and precisely determine the presence and/or location of disbonds in the structure caused by the tension shockwaves 50 induced by the wave induction tool 30. Accordingly, a non-destructive evaluation (NDE) process 12 is employed separate from and in addition to the conventional bond inspection process 10 in order to determine the presence of disbonds 60 in a structure 20 that has previously been inspected by the conventional bond inspection process. In other words, after completing the conventional bond inspection process 10 to verify the strength of a bond in a bonded structure, which includes steps (a)-(e) of FIG. 1, the separate NDE process, which includes steps (f) and (g) of FIG. 1, is initiated and completed. The end of the conventional bond inspection process 10 and the beginning of the NDE process 12 is demarcated by a dashed line in FIG. 1.

The conventional bond inspection process 10 and NDE process 12 are performed separately because the NDE process requires different environmental conditions and different testing equipment. Traditionally, the NDE process 12 is an ultrasound process conducted in a laboratory setting. The ultrasound process utilizes an ultrasound testing device 70 with a transmitter that transmits high-frequency acoustic waves 72 into the structure 20. The acoustic waves 72 reflect off features within the structure as reflected acoustic waves 74. The features tend to alter the characteristics of the acoustic waves such that the reflected acoustic waves 74 have different characteristics than the transmitted acoustic waves 72. The ultrasound testing device 70 also includes a receiver that detects the characteristics of the reflected acoustic waves 74. Further, the ultrasound testing device 70 includes logic that compares the characteristics of the reflected acoustic waves 74 to those of the transmitted acoustic waves 72. Based on the comparison, the ultrasound testing device 70 determines the presence or absence of disbonds in the structure 20. For example, in the illustrated embodiment, the characteristics of the reflected acoustic waves 74 in the structure 20 without disbonds (e.g., FIG. 1(f)) are different than the characteristics of the reflected acoustic waves 74 in the structure with a disbond 60 (e.g., FIG. 1(g)).

Often, for accurate and detailed results, the NDE process 12 includes immersing the structure 20 in an immersion tank filled with fluid (not shown) and transmitting and receiving the acoustic waves with a mobile, but non-handheld, ultrasound testing device 70 while the structure is immersed in the fluid. Movement of the ultrasound testing device 70 may be performed with precision mechanical motion control to scan across the structure and create images of the internal features of the structure. The fluid tends to enhance the transmission and reception of acoustic waves through the immersed structure 20 such that disbonds are more accurately detected. Some NDE processes 12 may include the use of mobile or handheld ultrasound testing devices 70. However, such mobile or handheld ultrasound testing devices 70 do not always provide adequately accurate and detailed results.

The need to either physically or chronologically separate performance of the conventional bond inspection process 10 and NDE process 12 into multiple testing procedures in order to detect the strength of and disbonds 60 within the structure 20 results in several disadvantages. For example, each process 10, 12 requires a separate testing setup and location in some instances, which increases the time and complexity for testing a bonded structure for strength and disbonds. Additionally, each of the processes 10, 12 require a pre-calibration step to calibrate the testing devices for use with various types and configurations of structures.

Figure 2:
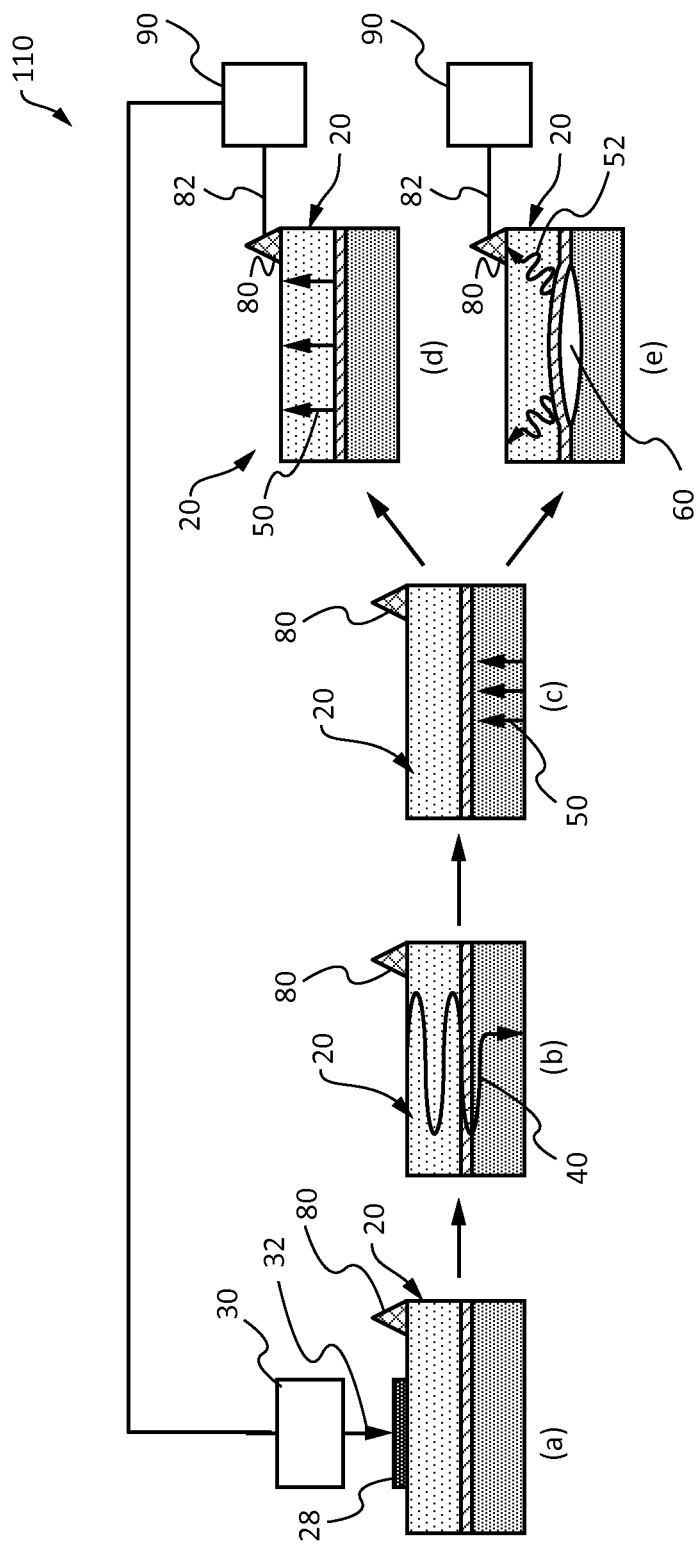
FIG. 2 is a schematic flow diagram of a combined laser bond and acoustic emission inspection process according to one embodiment.

Referring to FIG. 2, according to one embodiment, a bond inspection process 110 that concurrently detects the strength of and disbonds within a bonded structure in a single testing procedure is shown. Generally, the bond inspection process 110 integrates an acoustic emission technique into a laser bond inspection technique (or other shockwave induction technique) such that shockwaves in the structure induced by the laser bond inspection technique can be utilized to verify both the strength of the bond in the structure, as well as the presence of disbonds caused by the shockwaves. Accordingly, the bond inspection process 110 reduces the time, complexity, and effort required to verify the strength of and presence of disbonds in a bonded structure. Further, the acoustic emission technique in some implementations is self-calibrating, which also reduces time and effort associated with the pre-calibration steps of conventional bond inspection processes. As defined herein, concurrently may mean simultaneously, close proximity in time, during the same testing procedure, or using the same testing setup.

The structure 20 being tested by the bond inspection process 110 shares the same features as the structure being tested by the bond inspection process 10 described above. Further, the bond inspection process 110 is shown to utilize the same or similar type of wave induction tool 30 as used and described above in relation to the bond inspection process 10 except the wave induction tool 30 does not include or integrate a surface-velocity sensing device 34. Rather, in certain implementations, the wave induction tool 30 only generates and transmits a laser beam 32. Because a surface-velocity sensing device 34 is not integrated in the wave induction tool 30 of the process 10, the wave induction tool 30 can be smaller, and less complex than conventional wave induction tools.

In some embodiments, the bond inspection process 110 includes some of the same or similar steps or sub-processes as the bond inspection process 10 described above. For example, under the control of the controller 90, the wave induction tool 30 of the bond inspection process 110 induces a compression shockwave 40 in the structure via a laser beam 32. The compression shockwave 40 converts to a tension shockwave 50 that propagates through the structure 20 and for weaker bonds causes localized disbonds or delamination of the bonds, which results in disbond-induced acoustic waves 52.

Figure 3:
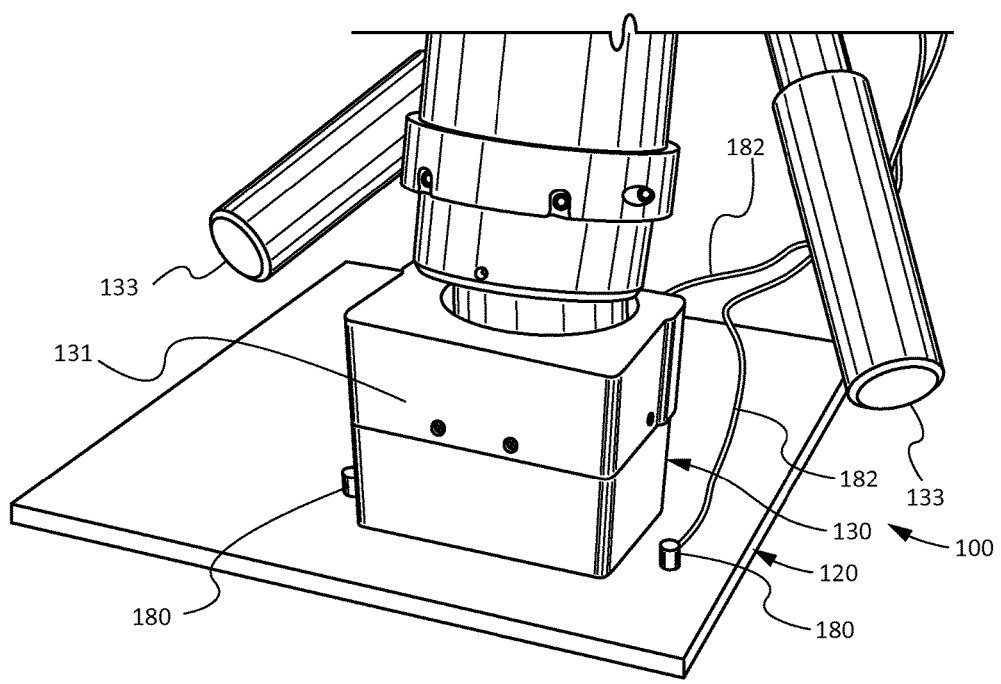
FIG. 3 is a perspective view of a laser bond tool and acoustic emission device of a bond inspection system according to one embodiment.

However, in contrast to the bond inspection process 10, the bond inspection process 110 utilizes an acoustic emission detection system that includes at least one acoustic emission sensor 80 positioned on a surface of the structure 20. The acoustic emission sensor 80 can be any of various sensors for detecting an acoustic emission propagating through the structure 20. According to some implementations, the acoustic emission sensor 80 is fixed secured on the surface of the structure 20, and is other implementations, the acoustic emission sensor is removably positioned on the surface of the structure. In another implementation, the acoustic emission sensor 80 is a piezoelectric sensor in contact with the surface of the structure 20. Referring to FIG. 3, in some implementations, the acoustic emission detection system includes more than one acoustic emission sensor as will be described in more detail below. The acoustic emission sensor 80 is electrically coupled to the controller 90 via an electrical communication line 82.

The acoustic emission sensor 80 is configured to detect the sound waves caused by the shockwaves 40, 50 induced in the structure by the wave induction tool 30. Generally, the shockwaves 40, 50 act as elastic stress waves that cause the structure 20 to undergo internal stress changes. When the internal stress from the tension shockwave is sufficiently high, a disbond occurs and acoustic energy is released forming ultrasound or high-frequency sound waves that propagate through the structure 20 in accordance with the shockwaves. Accordingly, the acoustic emission sensor 80 detects the shockwave-induced sound waves propagating through the structure 20 during the bond inspection process 110.

The sound waves detected by the acoustic emission sensor(s) 80 are transmitted to the controller 90, which, as will be described in more detail below, determines the presence or absence of disbonds based on the characteristics of the detected sound waves. In some implementations, the frequency characteristics of the sound waves correspond with the frequency characteristics of the shockwaves that induce the sound waves. For example, the frequency and magnitude of the sound waves are proportional to the frequency and magnitude of the shockwaves, which in turn depends on the characteristics of the structure. Accordingly, for a given frequency and magnitude of the shockwaves, which are controllable by the controller 90, the expected frequency and magnitude of the sound waves for a bonded structure with and without disbonds can be determined based on the known material and structural characteristics of the structure. In specific implementations, the frequency of the shockwaves is less than about 5 MHz. In certain implementations, the frequency of the shockwaves is between about 1 MHz and 10 MHz.

Because the strength of the bonded structure 20 is correlated to the presence or lack of disbonds 60 in the structure, the verification of a strength of the bond in the structure 20 occurs concurrently with the detection of sound waves by the acoustic emission sensor for determining the presence of disbonds or delamination along the bondline of the structure. In this manner, the bond inspection process 110 reduces the time, complexity, and effort required to determine the strength of a bonded structure and the presence of disbonds in the bonded structure, which may be formed during testing. In one implementation, the process 110 does not directly test the strength of the bonded structure 20, but rather verifies that a bond of the bonded structure is stronger or weaker than the shockwave pressures generated by the process. Although not shown, a separate NDE post-process similar to the NDE process 12 of FIG. 1 can be optionally performed after the bond inspection process 110 is conducted to provide an additional level of disbond detection.

According to one embodiment of a bond inspection system 100 shown in FIG. 3, the wave induction tool 30 used in the bond inspection process 110 can be a handheld, mobile wave induction tool 130. The wave induction tool 130 includes a head 131 that houses an energy transmission device (e.g., laser transmitter). Additionally, in certain implementations, the handheld wave induction tool 130 includes handles 133 for facilitating ease in manual operation of the tool and movement of the tool across a surface of a bonded structure 120 during testing of the structure.

The bond inspection system 100 also includes at least one acoustic emission sensor 180 positioned on, and in contact with, a surface of the structure 120. In the illustrated implementation, the system 100 includes two sensors 180. The acoustic emission sensors 180 are not directly coupled to the wave induction tool 130, and thus can be positioned at any of various locations on the structure 20. In this manner, the use of acoustic emission sensors 180 does affect the size of the head 131 of the wave induction tool 130, and thus the wave induction tool 130 can be smaller. In the illustrated implementation, the acoustic emission sensors 180 are spaced a desired distance apart from each other on the structure 120. The desired distance between the acoustic emission sensors 180 can be based on any of various factors. In one implementation, the desired distance between the acoustic emission sensors 180 is based on the size of the head 131 of the wave induction tool 130. For example, the desired distance should be wide enough to allow the head 131 to pass between the sensors 180 (e.g., wider than a width of the head 131). In some implementations, the desired distance corresponds with the distance resulting in an optimal detection of sound waves in the structure 120. For example, one of the acoustic emission sensors 180 is positioned a first distance away from an excitation region within the structure 20 (e.g., the region within the structure at which the laser beam 32 is directed), and another sensor is positioned a second distance away from the excitation region, which may be different than the first distance. Because the resultant tension shockwaves 50 and acoustic waves 52 are attenuated by the material of the bonded structure 20, acoustic emission sensors 180 positioned closer to the excitation region may provide more accurate readings or signals. In that implementation, the acoustic emission sensor(s) may become integrally mounted in the wave induction tool.

The acoustic emission sensors 180 can be fixedly or non-movably coupled to the surface of the structure 120 using any of various techniques, such as fasteners, adhesives, and the like. In some implementations, although the sensors 180 can be fixedly or non-movably coupled to the structure 120, the acoustic emission sensors 180 can be removably or temporarily coupled to the structure 120. In yet some implementations, the acoustic emission sensors 180 are not fixedly coupled to the structure 120 using coupling devices or materials, but are simply placed in contact with the structure and can move along the structure in the same manner as the head 131 of the wave induction tool 130.

The acoustic emission sensors 180 are electrically coupled to a controller (not shown) via respective electrical communication lines 182. Sound wave characteristics are detected by the acoustic emission sensors 180 and converted to acoustic emission signals including information or data representative of the characteristics of the sound waves. The acoustic emission signals are sent to the controller for processing via the electrical communication lines 182.

Figure 4:
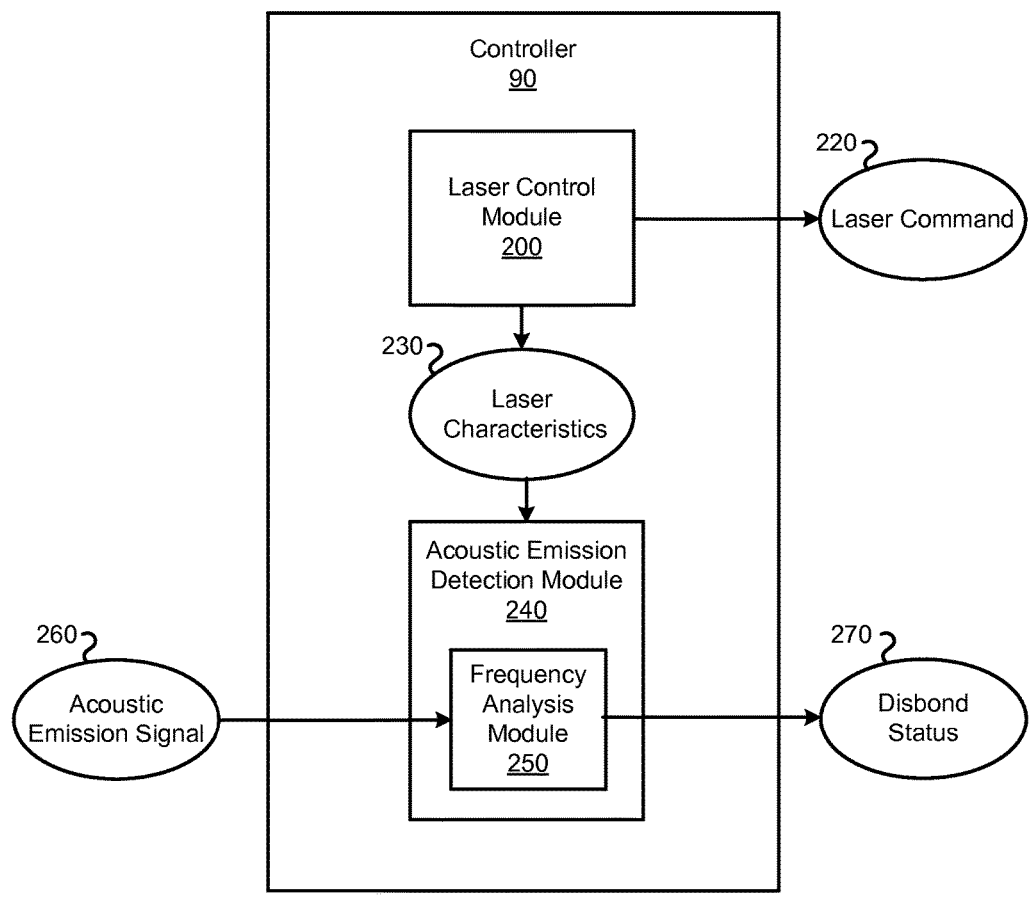
FIG. 4 is a schematic block diagram of a controller for a bond inspection system according to one embodiment.

According to one embodiment shown in FIG. 4, the controller 90 includes a laser bond inspection module 200 and an acoustic emission detection module 240. Generally, the laser bond inspection module 200 is configured to control the bond strength inspection process of the bond inspection process 110. The laser bond inspection module 200 is configured to generate a laser command 220 requesting from the wave induction tool 30 the generation and transmission of a laser beam 32 having the desired amplitude and pulse width characteristics demanded by the laser command 220. Accordingly, in some implementations, the laser command 220 includes a laser amplitude request and a laser pulse width request. The characteristics 230 of the laser beam 32 generated by the wave induction tool 30 may be communicated or known by the acoustic emission detection module 240 in certain implementations.

Generally, the acoustic emission detection module 240 is configured to monitor and detect the formation of disbonds in a structure during the bond inspection process 110, and in certain implementations, estimate a strength of the structure based on the detection of the formation of disbonds. After shockwaves are induced in the structure 20 by the wave induction tool 30, the acoustic emission detection module 240 receives an acoustic emission signal 260 from one or more acoustic emission sensors 80 in sound wave receiving communication with the structure. The acoustic emission signal 260 may include information regarding the amplitude and frequency of the sound waves detected by the sensors 80. Based on the acoustic emission signal 260, the acoustic emission detection module 240 determines a disbond status 270 of the structure 20. The disbond status 270 can be any of various indicators representing the presence or absence of a disbond 60 or delamination. For example, in one implementation, the disbond status 270 can be one of pass or fail. The pass status may indicate the absence of a disbond 60 (or the absence of notable disbonds), and the fail status may indicate the presence of a disbond (or the presence of notable disbonds). In yet some implementations, the disbond status 270 may indicate varying levels of severity of disbonds within the structure 20, such as low, high, or medium disbond severity.

Figure 5:
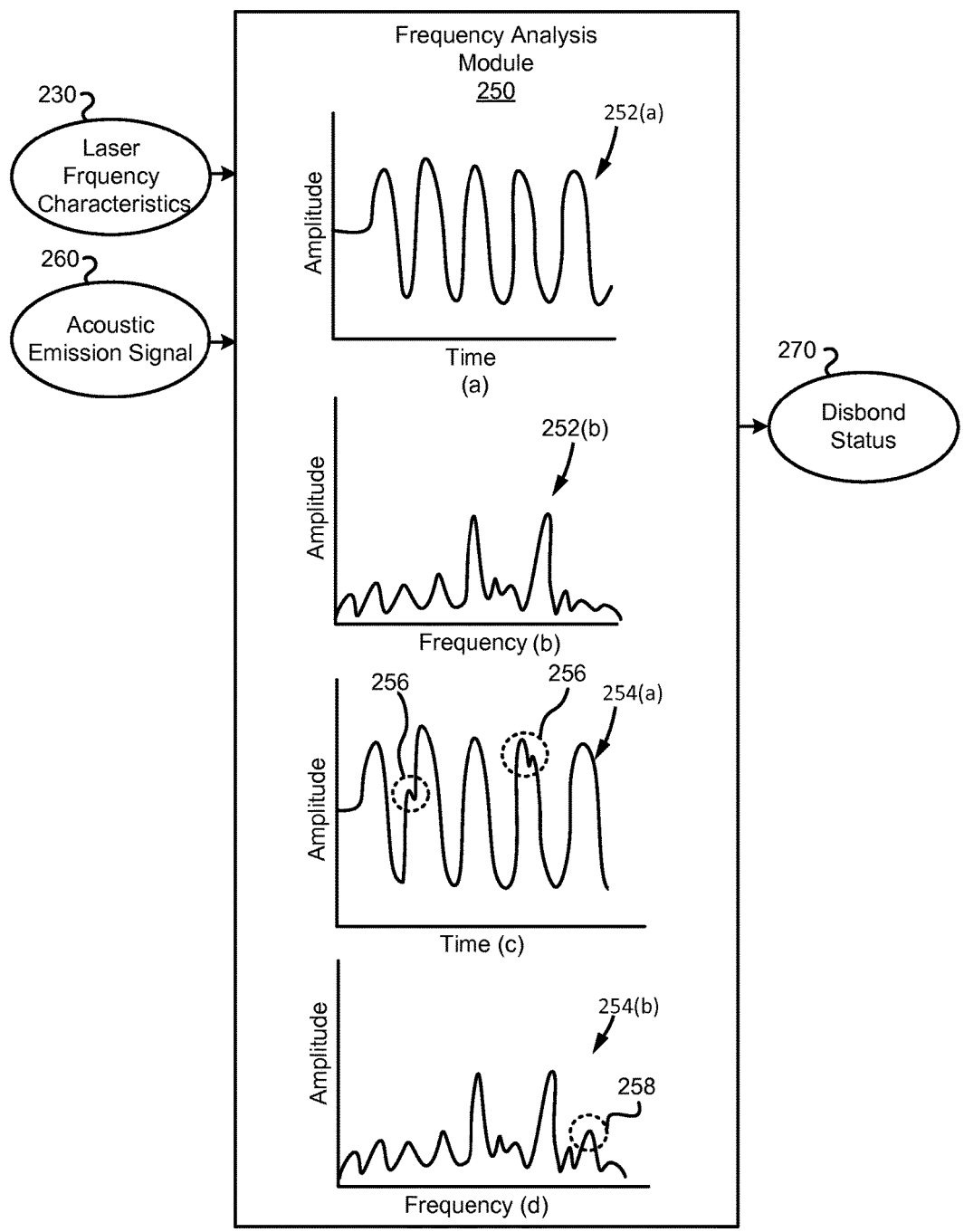
FIG. 5 is a schematic block diagram of a frequency analysis module of the controller of FIG. 4 according to one embodiment.

In some implementations, the disbond status 270 is determined by a frequency analysis module 250 of the acoustic emission detection module 240. Referring to FIG. 5, the frequency analysis module 250 receives laser characteristics 230 from the laser bond inspection module 200. Based on the laser characteristics 230, which as mentioned above may include the magnitude and pulse width of the laser beam 32, the frequency analysis module 250 estimates an expected frequency content pattern of the sound waves generated by the laser beam for a structure 20 without disbonds. The expected frequency content pattern can be an expected waveform pattern 252(a) (time vs. amplitude) and/or an expected Fast Fourier Transform (FFT) pattern 252(b) (frequency vs. amplitude) of the expected waveform pattern. One representation of an exemplary expected waveform pattern 252(a) and expected FFT pattern 252(b) is shown in FIG. 5. The expected frequency pattern 252 is shown on an amplitude-time chart 250(a). It is noted that the expected frequency content patterns 252(a) and (b) of FIG. 5 are merely examples of estimated frequency patterns, and that expected frequency patterns will vary based on the laser characteristics 230 and the properties of the structure 20.

The frequency analysis module 250 also receives the acoustic emission signal 260 from the acoustic emission sensor(s) 80. Based on the acoustic emission signal 260, which as mentioned above may include the amplitude and frequency of the sound waves detected by the sensor 80, the frequency analysis module 250 creates an actual frequency content pattern of the sound waves generated by the laser beam for the structure 20. According to one implementation, the frequency analysis module 250 creates an actual waveform pattern 254(a) and/or an actual FFT pattern 254(b) of the expected waveform pattern. One representation of an exemplary actual waveform pattern 254(a) and actual FFT pattern 254(b) is shown in FIG. 5. It is noted that the actual frequency content patterns 254(a) and (b) of FIG. 5 are merely examples of actual frequency content patterns, and that actual frequency content patterns will vary based on the laser characteristics 230 and the properties of the structure 20. In some implementations, the expected and actual frequency content patterns 252(a), 252(b), 254(a), 254(b) may be stored in memory of the controller 90.

In some embodiments, the frequency analysis module 250 compares at least one, and in some implementations, both, of the expected frequency content patterns 252a), 252(b) with the actual frequency content patterns 254(a), 254(b), respectively, to determine the disbond status 270. In one implementation, if the frequency analysis module 250 determines that the actual frequency content pattern(s) varies from the expected frequency pattern(s) by some threshold amount or in some way, the frequency analysis module will generate a disbond status 270 that indicates the presence of a disbond. However, if the frequency analysis module 250 determines that the actual frequency pattern(s) does not vary from the expected frequency pattern(s) by some threshold amount or in some way, the frequency analysis module will generate a disbond status 270 that indicates the absence of a disbond.

Generally, in some implementations, localized portions of the actual waveform pattern 254(a) exhibiting a change in frequency content may indicate the presence of a disbond. Because the frequency content of a sound wave propagating through a structure changes as the sound wave is reflected by a void created by a disbond, or the stress waves released by the disbonding process itself, have a unique frequency characteristic, changes in amplitude at distinct times will be present in the actual waveform pattern 254a). An additional frequency component(s) 256 is a change in the characteristic waveform that contains the frequency or frequencies that can be excited in the structure with no disbonds present. This change is typically at higher frequencies as indicated in FIG. 5 in comparison to the structural resonant frequency of the actual waveform pattern 254*a*). In some implementations, additional frequency components 256 in the actual waveform pattern 254(*a*) can be determined by the frequency analysis module 250 without comparison to, and estimation of, an expected waveform pattern 252(*a*). The distinctiveness of additional frequency components 256 can be enhanced in some implementations to improve the detectability of disbonds by adjusting the gain settings of the acoustic emission signal 260 or lowering the amplitude (e.g., energy) of the laser beam 32 such that the amplitude of the acoustic emission signal is correspondingly lowered. In some implementations, the distinctiveness of additional frequency components 256 can also be enhanced to improve the detectability of disbonds by the addition of conventional frequency bandpass filtering applied to the received signal or by the selection of an acoustic emission sensor 80 with response characteristics or sensitivity tailored to match the acoustic response characteristics of the bonded structure under test.

In addition, or alternative, to utilizing the actual waveform pattern 254(*a*) to determine the presence of disbonds in the bonded structure, the frequency analysis module 250 may utilize the actual FFT pattern 254(*b*) to determine the presence of disbonds in the structure. In certain implementations, the actual FFT pattern 254(*b*) may more clearly indicate the presence of additional frequency components 258 in the actual frequency content pattern sensed by the acoustic emission sensor(s) 80 of the process 110. As shown in FIG. 5, the additional frequency components 258 can appear as amplitude spikes or increases at one or more frequencies of the actual frequency content pattern compared to the expected frequency content pattern.

In some embodiments, the laser bond inspection module 200 is configured to conduct a low-high-low energy test by applying a low energy laser beam to the bonded structure, then a high energy laser beam to the bonded structure, followed by yet another low energy laser beam. Generally, if the intermediate application of high energy creates a disbond, then the first and last applications of low energy will be different in some way. Accordingly, the frequency analysis module 250 can be configured to compare the frequency patterns from the first and second applications of the low energy laser beams. In one implementation, if the frequency analysis module 250 determines that the frequency pattern from the second application of low energy varies from the frequency pattern from the first application of low energy by some threshold amount or in some way, the frequency analysis module will generate a disbond status 270 that indicates the presence of a disbond. However, if the frequency analysis module 250 determines that the frequency pattern from the second application of low energy does not vary from the frequency pattern from the first application of low energy by some threshold amount or in some way, the frequency analysis module will generate a disbond status 270 that indicates the absence of a disbond.

Figure 6:
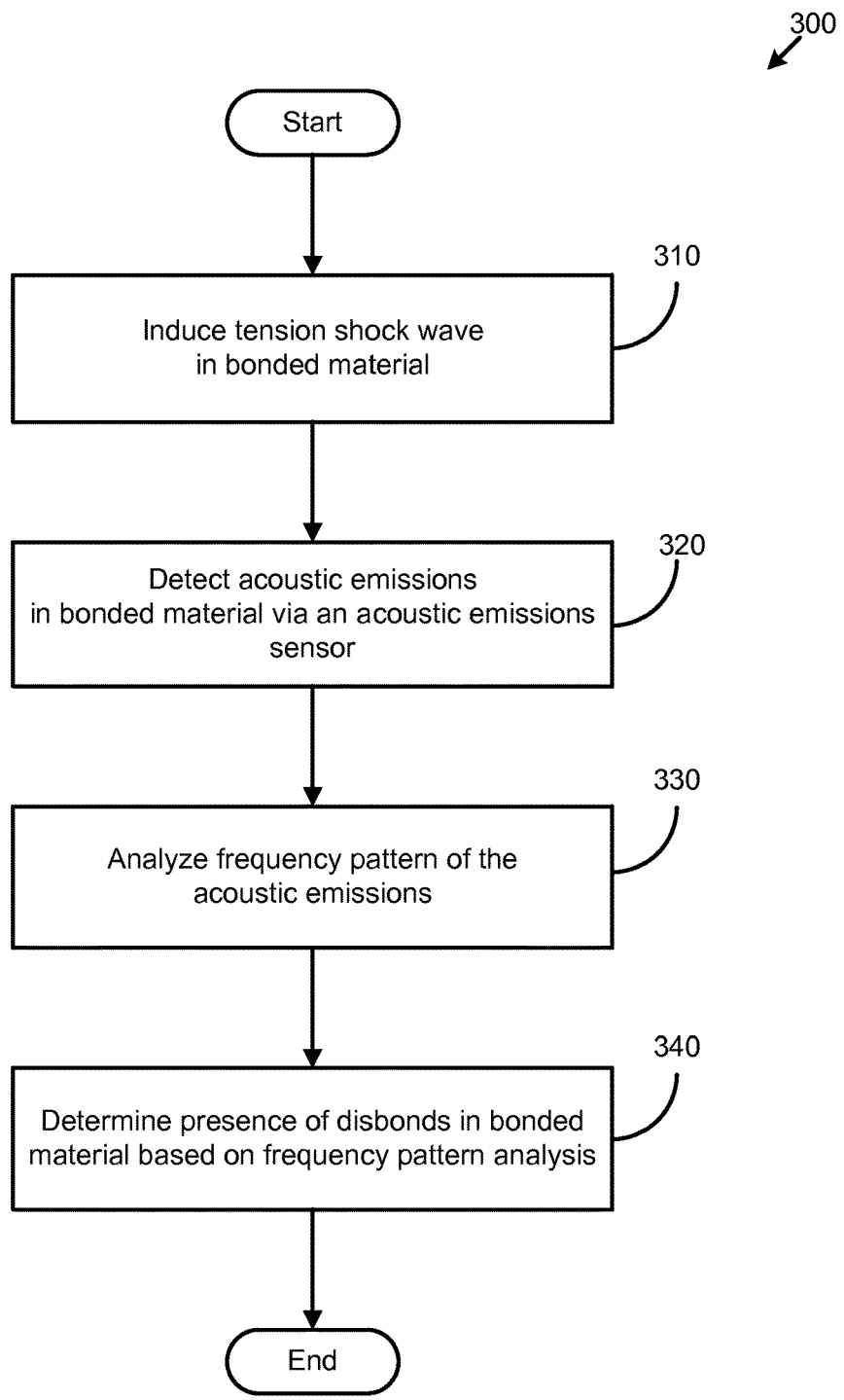
FIG. 6 is a schematic flow diagram of a method for concurrently inspecting the strength and defects of a bond of a structure.

Referring to FIG. 6, one embodiment of a method 300 for concurrently detecting the strength of and disbonds in a bonded material or structure includes inducing shockwaves in the bonded material at 310. The shockwaves can be induced using any of various techniques and devices. In one implementation, the induced shockwaves are tension shockwaves or compression shockwaves that convert into a tension shockwaves. With the shockwaves propagating through the bonded material, the method 300 includes detecting acoustic emissions in the bonded material at 320. The acoustic emissions can be detected at 320 with one or more acoustic emission sensors. As defined herein, the acoustic emission consists of sound waves generated or induced by the induced shockwaves. The method 300 further includes analyzing the frequency pattern of the detected acoustic emissions at 330. Analyzing the frequency pattern at 330 may include detecting anomalies, such as additional frequency components, in the frequency pattern, which may indicate the presence of a disbond. Based on the frequency pattern analysis conducted at 330, the method 300 includes determining the presence of disbonds in the bonded material at 340. For example, if additional frequency components are present in the frequency pattern as detected at 330, then determining the presence of disbonds at 340 includes indicating that at least one disbond is present in the bonded material.

Reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the subject matter of the present disclosure, however, absent an express correlation to indicate otherwise, an implementation may be associated with one or more embodiments.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s).

The computer readable medium may be a tangible computer readable storage medium storing the computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. Computer readable program code embodied on a computer readable signal medium may be transmitted using any appropriate medium, including but not limited to wireless, wireline, optical fiber cable, Radio Frequency (RF), or the like, or any suitable combination of the foregoing In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive.

What is claimed is:

1. A method for determining a presence of damage in a bond of a structure, comprising:
applying a first energy, a second energy, and a third energy comprising at least one laser beam to an excitation region of the structure with a wave form induction tool in slidable contact with a surface of the structure to induce first, second, and third tension shockwaves in the structure, wherein the second energy is a higher energy than the first energy and the third energy;
detecting first, second, and third sound waves caused by the first, second, and third tension shockwaves using at least two acoustic emission sensors in contact with the surface of the structure, the at least two acoustic emission sensors independent from one another and one of the at least two acoustic emission sensors is positioned a first distance apart from the excitation region and the other of the at least two acoustic emission sensors is positioned at a second distance apart from the excitation region, the first distance is different from the second distance, wherein the first energy, the second energy, and the third energy are applied at the surface of the structure at a position between the at least two acoustic emission sensors; and
determining the presence of damage in the bond of the structure due to the applied energy based on a comparison between the detected first and third sound waves and a variation between the first and third sound waves detected from the comparison.

2. The method of claim 1, wherein detecting the sound waves comprises detecting frequency characteristics of the sound waves, and determining the presence of damage in the structure is based on detected frequency characteristics of the sound waves.

3. The method of claim 2, wherein the frequency characteristics comprise a change in a characteristic frequency associated with the structure when no damage is present, and wherein the presence of the change in the characteristic frequency indicates damage in the structure.

4. The method of claim 1, further comprising estimating expected sound waves, and wherein determining the presence of damage in the structure comprises comparing the expected sound waves with detected sound waves.

5. The method of claim 4, wherein the expected sound waves are estimated based on characteristics of applied energy to the structure.

6. The method of claim 1, wherein the detected sound waves are analyzed to produce a Fast Fourier Transform pattern.

7. The method of claim 1, wherein at least one of the at least two acoustic emission sensors is slidable along the surface of the structure.

8. The method of claim 1, wherein applying energy to the structure induces compression shockwaves, and wherein the compression shockwaves convert into the tension shockwaves upon reflection off a surface of the structure.

9. The method of claim 1, further comprising assessing a minimal strength of the structure based on the determination of whether damage in the structure is present.

10. The method of claim 1, wherein the structure comprises a bonded structure, and wherein damage in the structure comprises delamination.

11. The method of claim 1, wherein the structure comprises first and second layers each made from a composite material or a composite material and a metal, and wherein damage is defined as separation of an adhesive layer between and adjoining the first and second layers.

12. The method of claim 1, wherein:
applying energy to the structure comprises applying a first low energy to the bonded structure to induce the first tension shockwaves, applying a second high energy to the bonded structure to induce the second tension shockwaves, and applying a third low energy to the bonded structure to induce the third tension shockwaves;
detecting sound waves comprises detecting the first sound waves caused by the first tension shockwaves, the second sound waves caused by the second tension shockwaves, and the third sound waves caused by the third tension shockwaves; and
determining the presence of damage in the bonded structure due to the applied energy comprises comparing the first sound waves to the third sound waves.

13. The method of claim 12, wherein a variation between a frequency pattern of the first sound waves and a frequency pattern of the third sound waves indicates the presence of damage in the bonded structure.

14. A system for concurrently determining strength of a bonded structure and presence of disbonds in the bonded structure, comprising: a wave induction tool that transmits a laser beam onto the bonded structure, when in slidable contact with a surface of the bonded structure, to induce first, second, and third shockwaves in the bonded structure, wherein the second shockwave is stronger than the first and third shockwave; a sound wave sensing device comprising at least two acoustic emission sensors that detects first, second, and third sound waves induced by the first, second, and third shockwaves, respectively, the sound wave sensing device being in direct contact with the surface of the bonded structure, the at least two acoustic emission sensors independent from one another and positioned a distance apart from each other on each side of the wave induction tool with at least one of the at least two acoustic emission sensors in slidable contact with the surface of the structure, wherein a first of the at least two acoustic emission sensors is a first distance away from a shockwave induction region in the bonded structure and a second of the at least two acoustic emission sensors is a second distance away from the shockwave induction region, wherein the first distance is different than the second distance, wherein the wave induction tool transmits the laser beam at a position on the surface between the at least two acoustic emission sensors; and a controller that determines the presence of disbonds in the bonded structure based on a variation of characteristics of the first and third sound waves detected by the sound wave sensing device, and determining the strength of the bonded structure based on the presence of disbonds in the bonded structure.

15. The system of claim 14, wherein the wave induction tool is slidable along the surface of the bonded structure and at least one of the at least two acoustic emission sensors of the sound wave sensing device is non-movably coupled to the surface of the bonded structure and positioned at a distance apart to allow the wave induction tool to pass between the at least two acoustic emission sensors of the source wave sensing device.

16. The system of claim 14, wherein the wave induction tool and the at least two acoustic emission sensors of the sound wave sensing device are in slidable contact with the surface of the bonded structure, and wherein the sound wave sensing device is integrally mounted in the wave induction tool.

17. The system of claim 14, wherein the strength of the bonded structure corresponds with a strength of the shockwave necessary to create a disbond in the bonded structure.

18. An apparatus for concurrently testing strength of a bonded structure and determining a presence of disbonds in the bonded structure, comprising:
- a laser bond inspection module configured to command a transmission of a laser beam, from a wave form induction tool in slidable contact with a surface of the bonded structure, onto an excitation region of the bonded structure to induce first, second, and third shockwaves in the bonded structure, wherein the second shockwave is stronger than the first and third shockwave;
- at least two acoustic emission sensors in contact with the surface of the bonded structure, the at least two acoustic emission sensors independent from one another and positioned in contact with the surface of the bonded structure a distance apart from each other with at least one of the at least two acoustic emission sensors positioned at a first distance from the excitation region and the other of the at least two acoustic emission sensors positioned at a second distance apart from the excitation region with the first distance being different from the second distance, wherein the energies are applied at the surface of the structure at a position between the at least two acoustic emission sensors; and
- an acoustic emission detection module configured to determine the presence of a disbond in the bonded structure and verify a strength of the bond based on at least one frequency characteristic of first, second, and third sound waves in the bonded structure induced by the first, second, and third shockwaves, respectively, the first, second, and third sound waves being detected by the at least one acoustic emission sensor.

19. The apparatus of claim 17, wherein the acoustic emission detection module is configured to determine the presence of a disbond in the bonded structure based on at least one characteristic of the laser beam transmitted onto the bonded structure.

* * * * *